United States Patent
Ogawa et al.

(10) Patent No.: US 10,302,604 B2
(45) Date of Patent: May 28, 2019

(54) SOLVENT DELIVERY DEVICE AND LIQUID CHROMATOGRAPH

(71) Applicant: SHIMADZU CORPORATION, Kyoto-shi, Kyoto (JP)

(72) Inventors: Keisuke Ogawa, Kyoto (JP); Yoshiaki Maeda, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 1560 days.

(21) Appl. No.: 13/783,922

(22) Filed: Mar. 4, 2013

(65) Prior Publication Data

US 2013/0233060 A1    Sep. 12, 2013

(30) Foreign Application Priority Data

Mar. 8, 2012    (JP) .................. 2012-051123

(51) Int. Cl.
  *G01N 30/34*    (2006.01)
  *G01N 30/50*    (2006.01)
  *G01N 30/24*    (2006.01)

(52) U.S. Cl.
  CPC ............ *G01N 30/50* (2013.01); *G01N 30/34* (2013.01); *G01N 30/24* (2013.01)

(58) Field of Classification Search
  CPC ............................. G01N 30/24; G01N 30/50
  USPC ............ 73/61.52, 863.01, 863.83; 210/198.2
  See application file for complete search history.

(56) References Cited

U.S. PATENT DOCUMENTS 4,696,183 A * 9/1987 Mitsumaki ........... G01N 33/492
                                              204/400

| | | | |
|---|---|---|---|
| 2006/0196282 | A1 | 9/2006 | Tatsumi et al. |
| 2010/0050737 | A1* | 3/2010 | Wolters ............ G01N 30/8665 73/23.22 |
| 2011/0209532 | A1* | 9/2011 | Maeda ..................... 73/61.56 |
| 2012/0031174 | A1 | 2/2012 | Aso |

(Continued)

FOREIGN PATENT DOCUMENTS

| | | |
|---|---|---|
| CN | 102507764 A | 6/2012 |
| JP | 64-059062 A | 3/1989 |
| JP | 02-124555 U | 10/1990 |

(Continued)

OTHER PUBLICATIONS

Office Action dated May 5, 2014, issued in corresponding Chinese Patent Application No. 201310066205.5, with English Translation (14 pages).

(Continued)

*Primary Examiner* — David Z Huang
(74) *Attorney, Agent, or Firm* — Westerman, Hattori, Daniels & Adrian, LLP

(57) ABSTRACT

A solvent delivery device includes a solvent delivery pump and a flow path switching valve. The flow path switching valve is connected to downstream ends of mobile phase sending flow paths and the solvent delivery pump is to be connected to one of the mobile phase sending flow paths by switching the flow path switching valve. At least one of the mobile phase sending flow paths includes a buffer solution sending flow path. The buffer solution sending flow path includes a butler solution storage section, a cleaning solution storage section, and a mobile phase switching valve for switching connection of the flow path switching valve to one of the storage sections.

4 Claims, 4 Drawing Sheets

(56) References Cited

U.S. PATENT DOCUMENTS

2012/0216632 A1    8/2012  Seki et al.

FOREIGN PATENT DOCUMENTS

| JP | 06-138112 A | 5/1994 |
| JP | 2002-14084 A | 1/2002 |
| WO | 2011/052445 A1 | 5/2011 |

OTHER PUBLICATIONS

Notification of Reason for Rejection dated Mar. 17, 2015, issued in corresponding Japanese Patent Application No. 2011-051123 with English translation (6 pages).
Office Action dated May 30, 2018, issued in counterpart Indian application No. 989/CHE/2013. (6 pages).

* cited by examiner

SOLVENT DELIVERY DEVICE AND LIQUID CHROMATOGRAPH

BACKGROUND OF THE INVENTION

1. Field of the Invention

The present invention relates to a solvent delivery device and a liquid chromatograph such as a high-performance liquid chromatograph (HPLC) and an ultra high-performance liquid chromatograph (UHPLC) for transferring a sample, injected into an analytical flow path by mobile phases sent by the solvent delivery device, to an analytical column, separating the sample into components, and detecting the respective separated components.

2. Description of the Related Art

As a solvent delivery device for sending mobile phases for transferring a sample, injected into an analytical flow path having an analytical column and a detector, to the analytical column and the detector, a gradient solvent delivery device is used in some cases. The gradient solvent delivery device is for sending the solution in the analytical flow path while changing composition of a mixed solution of a plurality of kinds of mobile phases with time (see Japanese Patent Application Laid-Open No. 2002-14084).

A structure of a liquid chromatograph including a low-pressure gradient solvent delivery device will be described by using FIG. 4.

The solvent delivery device 30 for supplying mobile phases to an analytical flow path 4 is provided and a sample injecting section 6, an analytical column 8, and a detector 10 are disposed on the analytical flow path 4. The sample injected by the sample injecting section 6 into the analytical flow path 4 is introduced into the analytical column 8 by the mobile phases sent by the solvent delivery device 30 and separated into respective components. The sample components separated in the analytical column 8 are transferred by the mobile phases to the detector 10 and detected.

The solvent delivery device 30 includes a solvent delivery pump 12 disposed on the analytical flow path 4 and a flow path switching valve 14 for switching between kinds of mobile phases pumped up by the solvent delivery pump 12. The flow path switching valve 14 includes four selective ports a to d disposed at a periphery portion and a central port disposed at a central portion and is formed to selectively connect any one of the selective ports to the central port. The analytical flow path 4 is connected to the central port of the flow path switching valve 14 and mobile phase sending flow paths 32, 34, 36, and 38 are respectively connected to the selective ports a, b, c, and d. The mobile phase sending flow paths 32, 34, 36, and 38 are flow paths for respectively sending liquid phases A, B, C, and D and a degasser 24 for degassing the mobile phases is provided on the flow paths 32, 34, 36, and 38.

The flow path switching valve 14 switches the flow path to be connected to the solvent delivery pump 12 according to time to thereby change composition of the mobile phase to be sent through the analytical flow path 4 by the solvent delivery pump 12.

In the conventional gradient solvent delivery device shown in FIG. 4, when the analysis ends and the solvent delivery pump 12 stops, the mobile phases remain in each flow path 32, 34, 36, and 38. For example, if the liquid phase A is an organic solvent and the liquid phase B is a high concentration buffer solution and when the mobile phases remain in the respective flow paths 32 and 34 after the end of the analysis, salt is liable to be precipitated at meeting portions of the flow paths in the flow path switching valve 14. If the salt is precipitated in the flow path switching valve 14, the flow paths are clogged to cause liquid leakage or the salt is pinched between a valve seat and a valve element of a solenoid valve forming the flow path switching valve 14 to cause failure of the solenoid valve.

SUMMARY OF THE INVENTION

It is, therefore, an object of the present invention to prevent precipitation of salt in the gradient solvent delivery device.

A solvent delivery device according to an aspect of the present invention includes a solvent delivery pump and a flow path switching valve for switching connection of one of flow paths to the solvent delivery pump. Downstream ends of mobile phase sending flow paths for respectively sending different kinds of mobile phases as the flow paths are connected to the flow path switching valve, and the solvent delivery pump is connected to one of the mobile phase sending flow paths by switching the flow path switching valve.

At least one of the mobile phase sending flow paths includes a buffer solution sending flow path for sending a buffer solution, and the buffer solution sending flow path includes a buffer solution storage section for storing the buffer solution, a cleaning solution storage section for storing a cleaning solution, and a mobile phase switching valve for switching connection of the flow path switching valve to one of the storage sections.

The solvent delivery device according to the present invention includes, as the mobile phase sending flow path, at least the buffer solution sending flow path for sending the buffer solution and further includes the mobile phase switching valve for switching connection of the buffer solution sending flow path to one of the buffer solution storage section for storing the buffer solution and the cleaning solution storage section for storing the cleaning solution. Therefore, after the analysis ends, it is possible to switch the upstream end of the buffer solution sending flow path to the cleaning solution storage section to send the cleaning solution from the buffer solution sending flow path. Accordingly, it is possible to prevent the buffer solution from remaining in the buffer solution sending flow path after the analysis ends to prevent precipitation of salt at meeting points in the flow path switching valve.

A liquid chromatograph according to an aspect of the present invention includes: an analytical flow path; a sample injecting section for injecting a sample into the analytical flow path; an analytical column provided on a downstream side of the sample injecting section on the analytical flow path to separate the sample into components; a detector for detecting the sample components separated in the analytical column; and the solvent delivery device according to the aspect of the present invention and for sending the mobile phases through the analytical flow path.

Because the liquid chromatograph according to the present invention includes, as the solvent delivery device for sending the mobile phase, the solvent delivery device, a trouble caused by the precipitation of the salt in the solvent delivery device does not occur and it is possible to accurately send the mobile phase, which increases reliability of a result of the analysis.

DETAILED DESCRIPTION OF THE INVENTION

A preferred embodiment of a solvent delivery device according to the present invention further includes a solvent delivery control section for controlling operations of a solvent delivery pump, a flow path switching valve, and mobile phase switching valves. The solvent delivery control section has a mobile phase sending means for carrying out a mobile phase sending operation by the solvent delivery pump and a cleaning means for connecting a buffer solution sending flow path to the solvent delivery pump, connecting the buffer solution sending flow path to a cleaning solution storage section after the mobile phase sending operation ends and carrying out a cleaning operation for sending a cleaning solution by the solvent delivery pump. In this way, after the analysis ends, the cleaning solution is sent through the buffer solution sending flow path and cleaning of the buffer solution sending flow path, an inside of the flow path switching valve, and an analytical flow path with the cleaning solution is carried out automatically.

Figure 1:
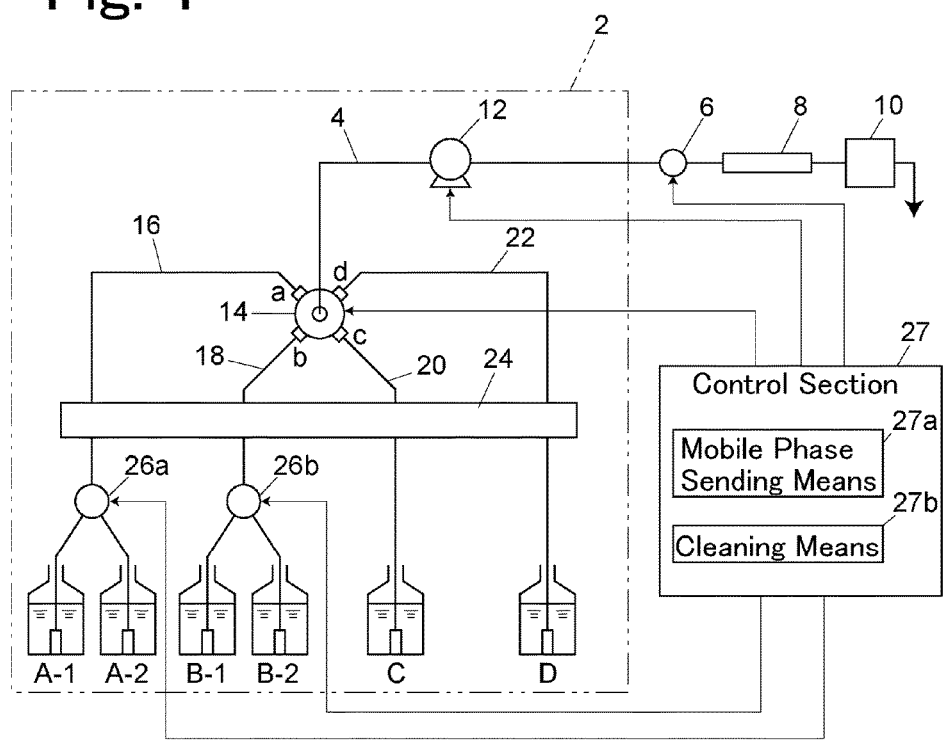
FIG. 1 is a schematic flow path block diagram showing an embodiment of a liquid chromatograph including a gradient solvent delivery device.

An embodiment of a liquid chromatograph including the low-pressure gradient solvent delivery device will be described by using FIG. 1.

The solvent delivery device 2 for supplying the mobile phase to the analytical flow path 4 is provided, and a sample injecting section 6, an analytical column 8, and a detector 10 are disposed on the analytical flow path 4. The sample injecting section 6 is an autosampler and the like for automatically injecting a sample into the analytical flow path 4. The sample injected by the sample injecting section 6 into the analytical flow path 4 is introduced into the analytical column 8 by a mobile phase from the solvent delivery device 2 and separated into respective components. The sample components separated in the analytical column 8 are further transferred to the detector 10 by the mobile phase from the solvent delivery device 2 and detected.

The solvent delivery device 2 is the low-pressure gradient solvent delivery device for changing composition of the mobile phase to be sent through the analytical flow path 4 with time. The solvent delivery device 2 includes a solvent delivery pump 12 disposed on the analytical flow path 4 and a flow path switching valve 14 for switching between kinds of mobile phases pumped up by the solvent delivery pump 12. The flow path switching valve 14 includes four selective ports a to d and one central port and is formed to selectively connect any one of the selective ports to the central port. The analytical flow path 4 is connected to the central port of the flow path switching valve 14. One end of a mobile phase sending flow path 16 is connected to the selective port a, one end of a mobile phase sending flow path 18 is connected to the selective port b, one end of a mobile phase sending flow path 20 is connected to the selective port c, and one end of a mobile phase sending flow path 22 is connected to the selective port d.

The other end of the mobile phase sending flow path 16 is connected by the mobile phase switching valve 26a to one of a vessel for storing the mobile phase A-1 and a vessel for storing a liquid phase A-2. The other end of the mobile phase sending flow path 18 is connected by the mobile phase switching valve 26b to one of a vessel for storing the mobile phase B-1 and a vessel for storing a liquid phase B-2. The other end of the mobile phase sending flow path 20 is connected to a vessel for storing a liquid phase C. The other end of the mobile phase sending flow path 22 is connected to a vessel for storing a liquid phase D. A degasser 24 for degassing the mobile phases is provided on the mobile phase sending flow paths 16, 18, 20, and 22.

Although the solutions prepared as the mobile phases are not especially limited, the mobile phases A-1 and B-1 are different kinds of high concentration buffer solutions and the liquid phases A-2 and B-2 are water as the cleaning solutions. The mobile phase sending flow path 16 serves as the buffer solvent delivery flow path for sending the buffer solution at the time of analysis of the sample and serves as a cleaning solvent delivery flow path for sending the cleaning solution when switched by the mobile phase switching valve 26a. The mobile phase sending flow path 18 functions in the same manner.

With this structure, it is possible to send the cleaning solutions from the mobile phase sending flow paths 16 and 18 to the analytical flow path 4 after the end of the analysis of the sample. If the buffer solutions remain in the mobile phase sending flow paths 16 and 18 after the analysis ends, salt may be precipitated at meeting points with an organic solvent in the flow path switching valve 14 to cause a trouble. However, by sending the cleaning solutions, the buffer solutions do not remain and it is possible to prevent precipitation of the salt.

It is, therefore, essential that the other end of the mobile phase sending flow path for sending the buffer solution can be connected to the vessel for storing the cleaning solution at the time of the analysis by the switching valve, and the mobile phase sent by the mobile phase sending flow path, which is not the mobile phase sending flow path for sending the buffer solution at the time of the analysis, may also be switched by the switching valve.

Figure 2:
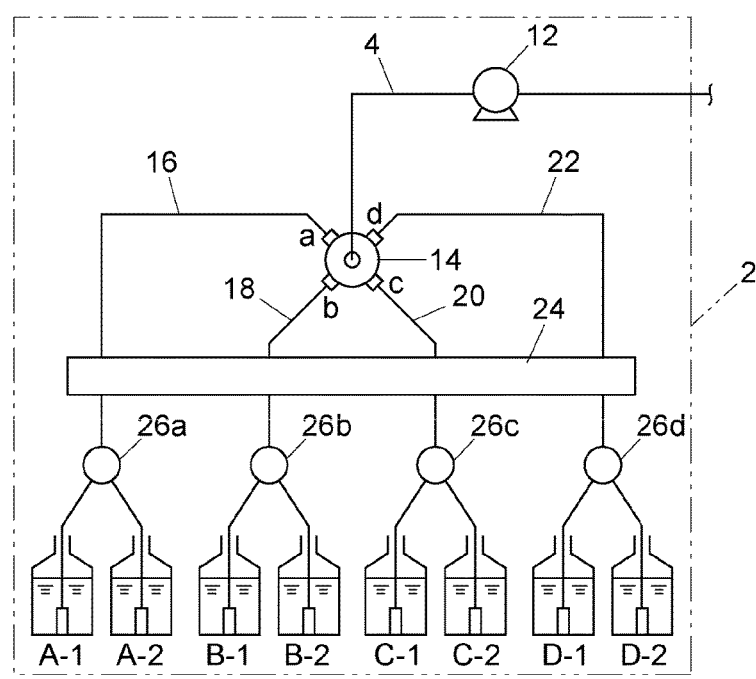
FIG. 2 is a schematic flow path block diagram showing another embodiment of the solvent delivery device.

In another embodiment shown in FIG. 2, the other end of the mobile phase sending flow path 16 can be connected to a vessel for storing cleaning water A-2 by the mobile phase switching valve 26a, the other end of the mobile phase sending flow path 18 can be connected to a vessel for storing cleaning water B-2 by the mobile phase switching valve 26b, the other end of the mobile phase sending flow path 20 can be connected to a vessel for storing cleaning water C-2 by a mobile phase switching valve 26c, and the other end of the mobile phase sending flow path 22 can be connected to a vessel for storing cleaning water D-2 by a mobile phase switching valve 26d. In this structure, after the analysis ends, it is possible to clean all of the mobile phase sending flow paths 16, 18, 20, and 22, flow paths in the flow path switching valve 14, and the analytical flow path 4.

Referring back to FIG. 1, driving of the sample injecting section 6, the solvent delivery pump 12, the flow path switching valve 14, and the mobile phase switching valves 26a and 26b is controlled by the control section 27. The control section 27 controls the sample injecting section 6 so that the sample is injected into the analytical flow path 4 according to a preset program. The control section 27 includes the mobile phase sending means 27a for carrying out gradient sending of the mobile phase by the solvent delivery device 2 at the time of the analysis of the sample. The mobile phase sending means 27a is formed to drive the solvent delivery pump 12 at the time of the analysis of the sample, switch the flow path switching valve 14 at predetermined time, and change the composition of the mobile phase to be sent through the analytical flow path 4 with time.

The control section 27 also includes a cleaning means 27b. The cleaning means 27b is formed to successively send the cleaning solutions A-2 and B-2 through the mobile phase sending flow paths 16 and 18 after the analysis of the sample ends. The control section 27 is a computer and may be implemented as a microcomputer system exclusively for the solvent delivery device or may be implemented by a computer for carrying out an operation of the liquid chromatograph mounted with the solvent delivery device and data processing. The control section 27 may be implemented by an external personal computer. The mobile phase sending means 27a and the cleaning means 27b are functions implemented by the computer.

Figure 3:
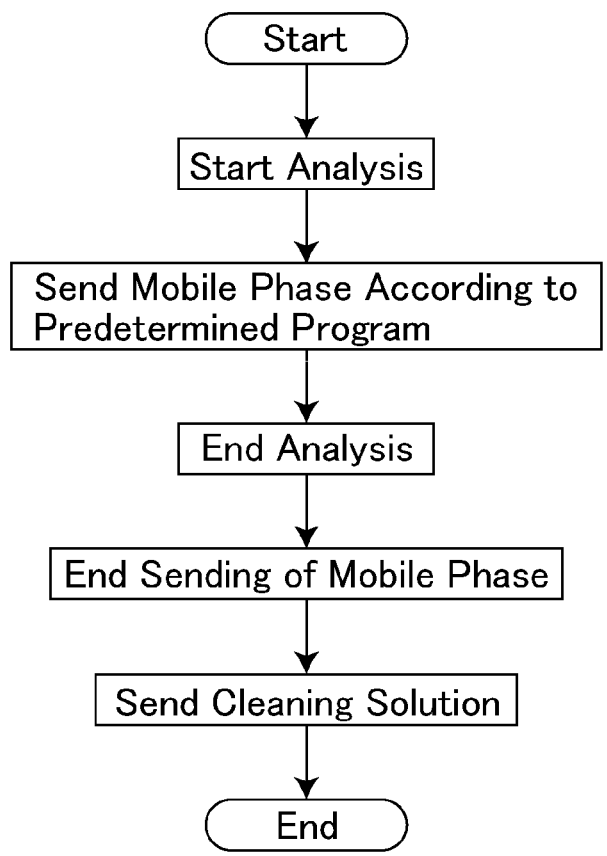
FIG. 3 is a flowchart for explaining operation of the embodiment.
Figure 4:
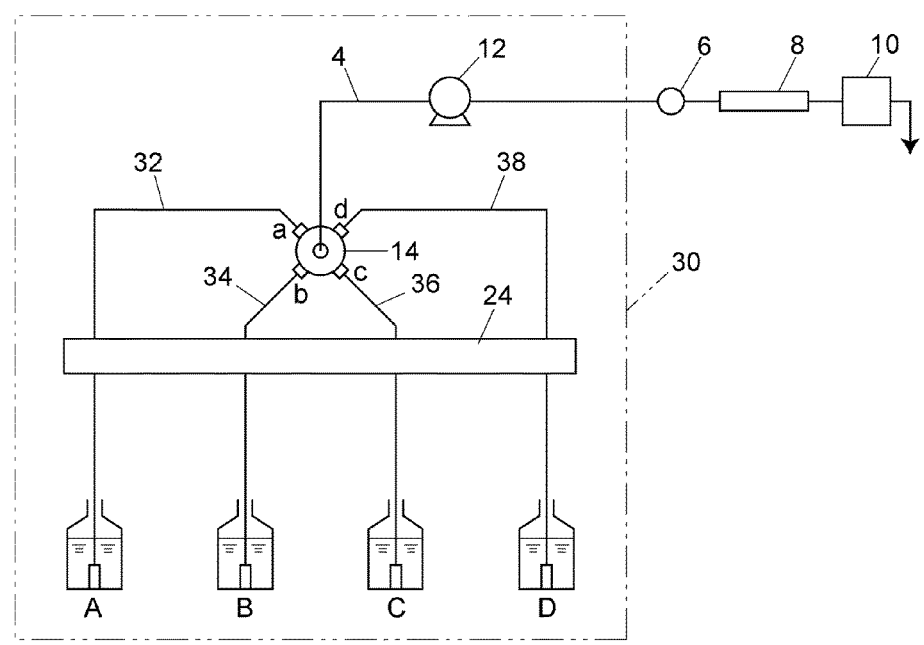
FIG. 4 is a schematic flow path block diagram showing an embodiment of a liquid chromatograph including a conventional gradient solvent delivery device.

The operation of the embodiment will be described by using a flowchart in FIG. 3.

When the analysis of the sample is started, the solvent delivery pump 12 is driven, the flow path switching valve 14 is switched at the preset timing, and the mobile phase is sent through the analytical flow path 4 while the composition of the mobile phase is changed with time. At this time, the mobile phase switching valve 26a selects the mobile phase A-1 and the mobile phase switching valve 26b selects the mobile phase B-1.

When the analysis ends, sending of the mobile phase for the analysis is stopped and the cleaning operation is carried out. The mobile phase switching valve 26a selects the liquid phase A-2 and the mobile phase switching valve 26b selects the liquid phase B-2. While the solvent delivery pump 12 is driven, the mobile phase sending flow path 16 and the mobile phase sending flow path 18 are successively connected to the analytical flow path 4, and the liquid phase A-2, which is the cleaning solution, is sent from the mobile phase sending flow path 16, and the liquid phase B-2, which is the cleaning solution, is sent from the mobile phase sending flow path 18 successively. The cleaning solutions A-2 and B-2 respectively sent from the flow paths 16 and 18 are discharged outside through the analytical flow path 4 and flow paths 16 and 18, the flow paths in the flow path switching valve 14, and the analytical flow path 4 are cleaned.

The cleaning operation may be carried out automatically when the analysis program ends or may be carried out for the first time when an analyst inputs a command for carrying out the cleaning operation to the control section 27.

The invention claimed is:

1. A solvent delivery device comprising a solvent delivery pump and a flow path switching valve for switching connection of one of a plurality of mobile phase sending flow paths to the solvent delivery pump, the flow path switching valve being connected to downstream ends of said mobile phase sending flow paths for respectively sending different kinds of mobile phases, wherein the solvent delivery pump is connected to one of the mobile phase sending flow paths by switching the flow path switching valve, wherein at least one of the mobile phase sending flow paths includes a buffer solution sending flow path for sending a buffer solution, wherein at least one of the mobile phase sending flow paths includes an organic solvent sending flow path for sending an organic solvent, and wherein the buffer solution sending flow path includes a buffer solution storage section for storing the buffer solution, a cleaning solution storage section for storing a cleaning solution, and a mobile phase switching valve for switching connection of the flow path switching valve to one of the storage sections.

2. The solvent delivery device according to claim 1 further comprising a solvent delivery control section for controlling operations of the solvent delivery pump, the flow path switching valve, and the mobile phase switching valve, wherein the solvent delivery control section includes a mobile phase sending means for carrying out a mobile phase sending operation by the solvent delivery pump, and a cleaning means for connecting the buffer solution sending flow path to the solvent delivery pump and connecting the buffer solution sending flow path to the cleaning solution storage section after the mobile phase sending operation ends and for carrying out a cleaning operation for sending the cleaning solution by the solvent delivery pump.

3. A liquid chromatograph comprising:
an analytical flow path;
a sample injecting section for injecting a sample into the analytical flow path;
an analytical column provided on a downstream side of the sample injecting section on the analytical flow path to separate the sample into components;
a detector for detecting the sample components separated in the analytical column; and
the solvent delivery device according to claim 1 for sending the mobile phases through the analytical flow path.

4. A liquid chromatograph comprising:
an analytical flow path;
a sample injecting section for injecting a sample into the analytical flow path;
an analytical column provided on a downstream side of the sample injecting section on the analytical flow path to separate the sample into components;
a detector for detecting the sample components separated in the analytical column; and
the solvent delivery device according to claim 2 for sending the mobile phases through the analytical flow path.

* * * * *